United States Patent [19]

Traber et al.

[11] 3,987,181

[45] Oct. 19, 1976

[54] CERTAIN 2-TRIFLUOROMETHYLBENZIMIDAZOLES AS ANTHELMINTICS

[75] Inventors: Walter Traber, Reinach; Ernst Aufderhaar, Augst, both of Switzerland

[73] Assignee: Ciba-Geigy Corporation, Ardsley, N.Y.

[22] Filed: Jan. 17, 1975

[21] Appl. No.: 541,980

[30] Foreign Application Priority Data

Jan. 22, 1974 Switzerland............................ 819/74

[52] U.S. Cl. ................................................ 424/273
[51] Int. Cl.² ........................................ A61K 31/415
[58] Field of Search .................................... 424/273

[56] References Cited
UNITED STATES PATENTS

| | | | |
|---|---|---|---|
| 3,506,767 | 4/1970 | Frick et al. ........................ | 424/273 |
| 3,749,734 | 7/1973 | Hannah et al. ..................... | 424/273 |
| 3,749,789 | 7/1973 | Fisher ................................ | 424/273 |

*Primary Examiner*—V. D. Turner
*Attorney, Agent, or Firm*—Harry Falber; Frederick H. Rabin

[57] ABSTRACT

Process for the control of parasitic helminths by the use of 2-trifluoromethyl-benzimidazole derivatives of formula I

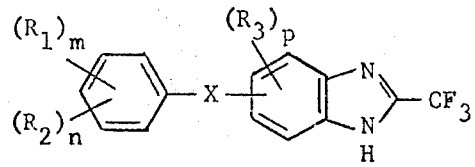

wherein
  $R_1$ represents halogen or a haloalkyl radical,
  $R_2$ represents halogen, an alkyl, alkenyl, alkoxy, alkenyloxy, alkylthio, alkenylthio, alkylsulphinyl, alkylsulphonyl, alkenylsulphinyl or alkenylsulphonyl radical,
  $R_3$ represents halogen,
  X represents oxygen, sulphur, sulphinyl or sulphonyl,
  m represents an integer from 0 to 3,
  n represents an integer from 0 to 2,
  p represents an integer from 0 to 3,
and salts thereof with inorganic or organic bases, and anthelmintic compositions containing a compound of the above formulae or a salt thereof.

7 Claims, No Drawings

CERTAIN 2-TRIFLUOROMETHYLBENZIMIDAZOLES AS ANTHELMINTICS

The present invention relates to the use of 2-trifluoromethyl benzimidazole derivatives for the control of helminths, and to compositions which contain such benzimidazoles.

The 2-trifluoromethyl-benzimidazoles usable according to the invention correspond to formula I

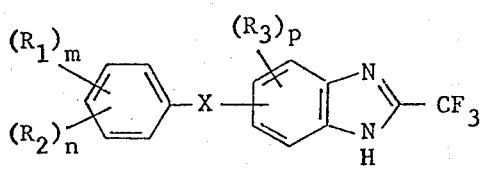

The symbols in this formula have the following meanings:

$R_1$ represents halogen or a haloalkyl radical,
$R_2$ represents halogen, an alkyl, alkenyl, alkoxy, alkenyloxy, alkylthio, alkenylthio, alkylsulphinyl, alkylsulphonyl, alkenylsulphinyl or alkenylsulphonyl radical,
$R_3$ represents halogen,
X represents oxygen, sulphur, sulphinyl or sulphonyl,
m represents an integer from 0 to 3,
n represents an integer from 0 to 2,
p represents an integer from 0 to 3.

The invention relates also to the salts of these compounds with inorganic or organic bases.

By halogen in formula I is meant, in particular, chlorine and bromine. The haloalkyl radical is preferably trifluoromethyl. Alkyl and alkenyl radicals can be straight-chain or branched-chain; they have preferably 1 to 4 carbon atoms in a straight chain. Those suitable are: methyl, ethyl, n-propyl, isopropyl, n-butyl, sec.butyl, tert.butyl and isobutyl; as well as, as an alkenyl radical, the allyl or methallyl radical. Such alkyl and alkenyl radicals constitute also the alkyl moiety and alkenyl moiety, respectively, of an alkoxy, alkylthio, alkenyloxy, alkenylthio, etc., radical.

The compounds of formula I are known (see British Patent Specification No. 1,151,471), and can be obtained by the process described therein; namely, by reaction of a suitable 1,2-phenylenediamine with a functional derivative of trifluoroacetic acid and/or with trifluoroacetic acid. Suitable for the preparation of salts are inorganic bases, especially alkali hydroxides, and organic bases.

Among the endoparasites occurring in warm-blooded animals, the helminths in particular do great harm. For example, animals infested by worms suffer not only inhibited growth but also, in some cases, such severe injury that the animals die. It is therefore of great importance that compositions be developed which are suitable for the control of helminths and of their development stages, and which can be used, if necessary, also for a preventive treatment against infestation by these parasites.

By "helminths" in the present description are meant parasitic nematodes, cestodes and trematodes of the gastrointestinal tract and of other organs.

2-trifluoromethyl-benzimidazoles have at different times in the literature been suggested as anthelmintics. In these compounds, the benzimidazole ring is substituted either partially or completely by chloride atoms, as is to be seen, e.g., from the German Offenlegungsschrift No. 2,016,622. On the other hand, trifluorobenzimidazoles of formula I having substitutions on the benzimidazole by phenoxy, phenylthio, phenylsulphinyl or phenylsulphonyl radicals have hitherto not been known as anthelmintics.

The benzimidazole derivatives of formula I are characterised by an excellent anthelmintic action against, for example:

nematodes — such as Ascaridae, Trichostrongylidae, Ancylostomatidae and Strongylidae;
cestodes — such as Anoplocephalidae and Taeniidae; and
trematodes — such as Fasciolidae and Schistosomatidae.

To be particularly emphasised is their action against Fasciolidae (*Fasciola hepatica*) and Trichostrongylidae (e.g., *Haemonchus contortus*).

For the compounds of formula I which are particularly preferred on account of their excellent biological effectiveness there apply the definitions given under formula I, with the limitation that the radical bound by way of X on the benzimidazole is in the 5- or 6-position, and p represents 3.

Examples of such compounds of formula I are:

| | |
|---|---|
| 2-trifluoromethyl-6-(3',4'-dichlorophenoxy)-4,5,7-trichlorobenzimidazole | M.P. 220–222° C, |
| 2-trifluoromethyl-4,6,7-trichloro-5-(4'-bromophenoxy)-benzimidazole | M.P. 228–230° C, |
| 2-trifluoromethyl-5-(4'-chlorophenylsulphonyl)-4,6,7-trichlorobenzimidazole | M.P. 168–173° C. |

Also the following 2-trifluoromethyl-benzimidazoles of formula I, for example, have a good anthelmintic action:

| | |
|---|---|
| 2-trifluoromethyl-4-(3',4'-dichlorophenoxy)-5,7-dichlorobenzimidazole | M.P. 116–118° |
| 2-trifluoromethyl-4-(4'-chlorophenoxy)-5,7-dichlorobenzimidazole | M.P. 205–207° |
| 2-trifluoromethyl-4-(2',4'-dichlorophenoxy)-5,7-dichlorobenzimidazole | M.P. 194–196° |
| 2-trifluoromethyl-4-phenoxy-5,7-dichlorobenzimidazole | M.P. 204–206° |
| 2-trifluoromethyl-4-(3'-trifluoromethyl-4'-chlorophenoxy)-5,7-dichlorobenzimidazole | M.P. 199–201° |
| 2-trifluoromethyl-4-phenylthio-5,7-dichloro- | M.P. 177–179° |

-continued

| Compound | M.P. |
|---|---|
| benzimidazole | |
| 2-trifluoromethyl-4-(4'-chlorophenylthio)-5,7-dichlorobenzimidazole | M.P. 218–220° |
| 2-trifluoromethyl-4-(4'-chlorophenyl-sulphinyl)-5,7-dichlorobenzimidazole | |
| 2-trifluoromethyl-4-(4'-chlorophenyl-sulphonyl)-5,7-dichlorobenzimidazole | M.P. 238–240° |
| 2-trifluoromethyl-4-(4'-chlorophenoxy)-5,7-dichloro-6-bromobenzimidazole | |
| 2-trifluoromethyl-4-(4'-bromophenoxy)-5,7-dichlorobenzimidazole | M.P. 201–203° |
| 2-trifluoromethyl-4-(4'-bromophenoxy)-5,7-dichloro-6-bromobenzimidazole | |
| 2-trifluoromethyl-6-(3',4'-dichlorophenoxy)-5-chlorobenzimidazole | M.P. 238–240° |
| 2-trifluoromethyl-6-(4'-chlorophenylthio)-5-chlorobenzimidazole | M.P. 212–214° |
| 2-trifluoromethyl-4-(4'-methoxyphenoxy)-5,7-dichlorobenzimidazole | M.P. 186–188° |
| 2-trifluoromethyl-4-(2',4',5'-trichlorophenoxy)-5,7-dichlorobenzimidazole | M.P. 150–152° |
| 2-trifluoromethyl-5-(3',4'-dichlorophenoxy)-6-chlorobenzimidazole | M.P. 238–240° |
| 2-trifluoromethyl-5-(3'-trifluoromethyl-4'-chlorophenylthio)-6-chlorobenzimidazole | M.P. 208–210° |
| 2-trifluoromethyl-5-(4'-chlorophenylthio)-6-chlorobenzimidazole | M.P. 212–214° |
| 2-trifluoromethyl-s-(2',4',5'-trichlorophenoxy)-6-chlorobenzimidazole | M.P. 225–227° |
| 2-trifluoromethyl-5-(2',5'-dichlorophenylthio)-6-chlorobenzimidazole | M.P. 182–184° |
| 2-trifluoromethyl-5-(4'-chlorophenoxy)-6-chlorobenzimidazole | M.P. 191–193° |
| 2-trifluoromethyl-5-(4'-methoxy-phenoxy)-6-chlorobenzimidazole | M.P. 178–180° |
| 2-trifluoromethyl-5-(3'-trifluoromethyl-phenoxy)-6-chlorobenzimidazole | M.P. 191–193° |
| 2-trifluoromethyl-5-(4'-bromophenoxy)-6-chlorobenzimidazole | M.P. 196–198° |
| 2-trifluoromethyl-4-(3',4'-dichlorophenoxy)-5,6,7-trichlorobenzimidazole | 140° with decomp. |
| 2-trifluoromethyl-4-(3'-trifluoromethyl-4'-chlorophenylsulphonyl)-5,6,7-trichloro-benzimidazole | M.P. 254–256° |
| 2-trifluoromethyl-4-bromo-5-(4'-bromophenoxy)-6-chlorobenzimidazole | M.P. 219–220° |
| 2-trifluoromethyl-4,6-dichloro-5-(4'-bromo-phenoxy)-benzimidazole | M.P. 210–212° |
| 2-trifluoromethyl-5-(4'-bromophenylthio)-6-chlorobenzimidazole | M.P. 205–207° |
| 2-trifluoromethyl-5-(4'-bromophenyl-sulphonyl)-6-chlorobenzimidazole | M.P. 124–126° |
| 2-trifluoromethyl-5-(4'-chlorophenoxy)-benzimidazole | M.P. 209–210° |
| 2-trifluoromethyl-5-(4'-bromophenoxy)-benzimidazole | M.P. 211–213° |
| 2-trifluoromethyl-5-(4'-methoxy-phenoxy)-benzimidazole | M.P. 147–150° |
| 2-trifluoromethyl-4-(3'-chlorophenoxy)-5,7-dichlorobenzimidazole | M.P. 190–192° |
| 2-trifluoromethyl-4-(2',5'-dichlorophenyl-thio)-5,7-dichlorobenzimidazole | M.P. 198–200° |
| 2-trifluoromethyl-4-(3'-trifluoromethyl-phenoxy)-5,7-dichlorobenzimidazole | M.P. 177–179° |
| 2-trifluoromethyl-4-(4'-chloro-3-trifluoro-methyl-phenylthio)-5,7-dichlorobenzimidazole | M.P. 175–177° |
| 2-trifluoromethyl-5-phenylthio-6-chloro-benzimidazole | M.P. 222–224° |
| 2-trifluoromethyl-5-(3'-trifluoromethyl-4'-chlorophenoxy)-6-chlorobenzimidazole | M.P. 263–265° |
| 2-trifluoromethyl-5-phenoxy-6-chloro-benzimidazole | M.P. 205–207° |
| 2-trifluoromethyl-6-(4'-chlorophenyl-sulphinyl)-5-chlorobenzimidazole | |
| 2-trifluoromethyl-6-(4'-chlorophenyl-sulphonyl)-5-chlorobenzimidazole | M.P. 101–104° |
| 2-trifluoromethyl-6-(4'-chlorophenylthio)-4,7-dibromobenzimidazole | |
| 2-trifluoromethyl-6-(4'-chlorophenyl-sulphonyl)-4,7-dibromo-5-chlorobenzimidazole | |
| 2-trifluoromethyl-6-(4'-bromophenoxy)-5-chlorobenzimidazole | M.P. 196–198° |
| 2-trifluoromethyl-6-(3'-trifluoromethyl-4-chlorophenoxy)-5-chlorobenzimidazole | M.P. 208–210° |
| 2-trifluoromethyl-4-(4'-chlorophenoxy)-5-fluorobenzimidazole | |

The anthelmintic effectiveness of the 2-trifluoromethylbenzimidazoles of formula I is demonstrated by means of the following tests:

1. Tests on Mice Infested by Oxyuris

The active substances are administered in the form of a suspension, by means of a stomach probe, to white mice infested with mouse oxyuris (threadworms). Five animals are used for each test. The active substances are administered to each group of animals once daily during three successive days. The daily dose per animal is 100 mg of active substance per kg of body weight.

The animals are then killed on the 4th day after commencement of the treatment and dissected. After dissection of the test animals, an evaluation is made by a comparison of the number of mouse oxyuris remaining in the intestines with the number remaining in the intestines of untreated control animals which have been identically and simultaneously infested.

2. Tests on Mice Infested by *Nippostrongylus Brasiliensis*

The active substances are administered in the form of a suspension by means of a stomach probe to white mice infested with *Nippostrongylus brasiliensis*. Five animals are used for each test. The active substances are administered to each group of animals once daily during three successive days. The daly dose for each animals is 100 mg of active substance per kg of body weight.

The animals are then killed on the fourth day after commencement of the treatment and dissected. After dissection of the test animals, an evaluation is made by comparison of the number of parasites remaining in the intestines with the number remaining in the intestines of untreated control mice that have been identically and simultaneously infested.

3. Tests on Mice Infested by *Hymenolepis Nana*

The active substances are administered in the form of a suspension by means of a stomach probe to white mice artificially infested with *Hymenolepis nana*. Five animals are used for each test. The active substances are administered to each group of animals once daily during three successive days. The animals are then killed on the fourth day after commencement of the treatment and dissected. After dissection of the test animals, an evaluation is made by comparison of the number of tapeworms present in the intestines with the number present in the intestines of untreated control mice that have been identically and simultaneously infested.

4. Tests On Rats Infested By *Fasciola Hepatica*

White laboratory-rats are infested with common liver flukes (*Fasciola hepatica*). After expiration of the prepatent period, three infested rats per test are each treated once daily on three successive days with the active substance, which is administered in the form of a suspension by stomach probe. Two weeks after administration of the active substance, the test animals are killed and examined to determine the number of common liver flukes present.

Particularly the 2-trifluoromethyl-benzimidazoles of formula I wherein X stands for oxygen or sulphur were distinguished in these tests by their extremely high level of effectiveness and compatibility. To be emphasised is the excellent action of these phenoxy- and phenylthio-2-trifluoromethyl-benzimidazoles against *Fasciola hepatica*.

The compositions according to the invention are used for the control of parasitic helminths in the case of domestic and farm animals, such as cattle, sheep, goats, horses, pigs, cats, dogs and poultry. They can be administered in single doses to the animals, or in repeated doses, the single doses being, depending on the species of animals, preferably between 0.5 and 100 mg per kg of body weight. A better effect can be obtained in some cases by a protracted administration of the active substances, or smaller complete doses may be sufficient. The active substances or mixtures containing them can also be added to the feed or be introduced into drinking troughs. The finished feed contains the substances of formula I preferably at a concentration of 0.005 to 0.1 per cent by weight. The compositions can be administered to the animals, perorally or via the abomasum, in the form of solutions, emulsions, suspensions (drenches), powders, tablets, boluses and capsules. These preparations are obtained by the use, for example, of customary solid carriers, such as kaolin, talcum, bentonite, sodium chloride, calcium phosphate or cottonseed meal, or by the use of liquids that do not react with the active substances, such as oils and other solvents and diluents harmless to the animal organism. Provided that the physical and toxicological properties of solutions and emulsions permit it, the active substances can be injected into the animals, for example, subcutaneously.

If the anthelmintic agents are in the form of feed concentrates, then the carriers used are, for example, hay, production feed, fodder grain or protein concentrates. These feed concentrates can contain, in addition to the active substances, also additives, vitamins, antibiotics, chemotherapeutical agents, or other pesticides, mainly bacteriostatics, fungistatics or coccidiostatics, and also hormone preparations, substances having anabolic activity, or other substances promoting growth, affecting the quality of the meat of slaughter cattle, or being in some other way beneficial for the organism. They may also be combined with other anthelmintics, by virtue of which their action is broadened and adapted to suit given circumstances. The following other anthelmintics are to be mentioned:

Nematocides: e.g., Absonal, Alcopar, Anthelcide, Ascaridole, Badminth II, Bethenium, Bradosol, Cambendazol, Chlorophos, Chlorthion, Coumaphos, Cyanin, Destomycin, Diethylcarbamazine, Dichlorophene, DDVP, 1,4-di-(D-glyconyl)-piperazine, Dithiazonine, Dow ET/70, Dowco 132, Dymanthine HCl, Egressin, Gainex, Hexachlorophene, Hexylresorcinol, Ionit, Levamisol, Mepacrine, Methylene violet, 1-Methyl-1-tridecylpiperazinium-4-carboxylic acid ethyl ester, Methyridine, Monopar, Narlene, Neguvon, Nematodin, Nemural, Nidanthel, Parbendazol, Parvex, Phenothiazine, Piperazine, Polymethylene-piperazine, Promethazine, Pyrantel, Pyranthiazine, Pyrvinium-embonate, Rametin, Ronnel, Santonin, Shell 1808, Stilbazium, Tetramisole, Thenium, Thiabendazole, Thymolan, Vermella and Mebendazol;

cestocides: e.g. Acranil, Arecoline, Atebrin, Bithionol, Bithionol oxide, Bunamidine, Cestodin, Cambendazol, Dibutyltin dilaurate, Dichlorophen, Dioctyltin dichloride, Dioctyltin laurate, Filixic acid, Hexachlorophene, Nidanthel, Terenol and Yomesan.

Anthelmintic agents according to the invention are produced in a manner known per se by the intimate mixing and grinding of active substances of the general formula I with suitable carriers, optionally with the addition of dispersing agents or solvents which are inert to the active substances.

The active substances can be obtained and used in the following forms:

solid preparations: dusts, granulates, coated granulates, impregnated granulates and homogeneous granulates;
water-dispersible concentrates of active substance:
liquid preparations: solutions or pastes (emulsions).

The particle size of the carriers is advantageously up to about 0.1 mm for dusts and wettable powders, and 10–500 μ (0.001–0.5 mm) for granulates.

The concentration of active substance in the solid preparations is from 0.5 to 80 percent, and in the liquid preparations it is from 0.5 to 15 percent.

To these mixtures there may also be added additives stabilizing the active substance, and/or nonionic, anion-active and cation-active substances, which, for example, ensure a better degree of wettability (wetting agents) and dispersibility (dispersing agents).

Water-dispersible powder mixture

Composition:

| Water-dispersible powder mixture Composition: | |
|---|---|
| 25 | parts of 2-trifluoromethyl-4,6,7-trichloro-5-(4'-bromophenoxy)-benzimidazole, |
| 3 | parts of a mixture of polyoxyethylene/tall oil ester/urea, |
| 7 | parts of polyvinylpyrrolidone, |
| 31.5 | parts of highly dispersed silicic acid, |
| 33.5 | parts of bolus alba. |

The active substance is homogeneously mixed, in a planetary mixer, together with the polyoxyethylene/tall oil ester/urea mixture and polyvinylpyrrolidone, with the addition of about 30 percent of the amount of silicic acid. The remaining portion of silicic acid and the bolus alba are subsequently added, and the whole is mixed in suitable mixers until homogeneity is obtained. The mixture is then ground in a dowelled disk mill until the particle size is below 20 microns.

We claim:

1. A process for the control of parasitic helminths in warm blooded animals which comprises administering orally or subcutaneously to the animal an anthelmintically effective amount of a 2-trifluoromethylbenzimidazole compound of formula I

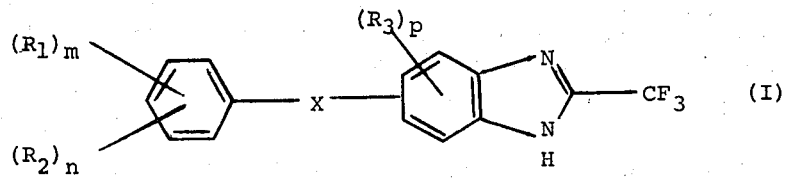

wherein
$R_1$ represents halogen or trifluoromethyl,
$R_2$ represents halogen, $C_1$–$C_4$ alkyl, $C_3$–$C_4$ alkenyl, $C_1$–$C_4$ alkoxy, $C_3$–$C_4$ alkenyloxy, $C_1$–$C_4$ alkylthio, $C_3$–$C_4$ alkenylthio, $C_1$–$C_4$ alkylsulphinyl, $C_1$–$C_4$ alkylsulphonyl, $C_3$–$C_4$ alkenylsulphinyl or $C_3$–$C_4$ alkenylsulphonyl,
$R_3$ represents halogen,
X represents oxygen, sulphur, sulphinyl or sulphonyl,
$m$ represents an integer from 0 to 3,
$n$ represents an integer from 0 to 2,
$p$ represents an integer from 0 to 3,
or salts thereof with inorganic or organic bases.

2. The process according to claim 1, wherein in said compound of formula I the radical bound by way of X on the benzimidazole is in the 5- or 6-position, and p represents 3.

3. The process according to claim 1, wherein said compound is 2-trifluoromethyl-6-(3', 4'-dichlorophenoxy)-4,5,7-trichlorobenzimidazole.

4. The process according to claim 1, wherein said compound is 2-trifluoromethyl-4,6,7-trichloro-5-(4'-bromophenoxy)-benzimidazole.

5. The process according to claim 1, wherein said compound is 2-trifluoromethyl-5-(4'-chlorophenylsulphonyl)-4,6,7-trichlorobenzimidazole.

6. The process according to claim 1 wherein in said compound X represents oxygen or sulphur.

7. The process of claim 1, wherein parasitic trematodes are controlled by said compounds.

* * * * *